United States Patent [19]
Manirazman

[11] Patent Number: 5,817,299
[45] Date of Patent: Oct. 6, 1998

[54] NON-CHEMICAL SUNSCREEN COMPOSITION

[75] Inventor: Abul M. Manirazman, Port Jefferson, N.Y.

[73] Assignee: E-L Management Corp., New York, N.Y.

[21] Appl. No.: 742,300

[22] Filed: Nov. 1, 1996

[51] Int. Cl.⁶ .............................. A61K 7/42; A61K 7/00; A61K 35/78

[52] U.S. Cl. ......................... 424/59; 424/400; 424/401; 424/195.1

[58] Field of Search ............................ 424/59, 400, 401, 424/195.1

[56] References Cited

U.S. PATENT DOCUMENTS

| | | | |
|---|---|---|---|
| 3,436,407 | 4/1969 | Masquelier | 549/400 |
| 4,698,360 | 10/1987 | Masquelier | 514/456 |
| 5,256,404 | 10/1993 | Martino et al. | 424/59 |
| 5,470,874 | 11/1995 | Lerner | 514/474 |
| 5,484,594 | 1/1996 | Frangi et al. | 424/195.1 |
| 5,552,135 | 9/1996 | Cioca et al. | 424/59 |

FOREIGN PATENT DOCUMENTS

| | | |
|---|---|---|
| 63-267774 | 11/1988 | Japan . |
| 01042479 | 2/1989 | Japan . |
| 06049053 | 2/1994 | Japan . |
| WO 9013304 | 11/1990 | WIPO . |

OTHER PUBLICATIONS

The Second International; Pycnogenol Symposium, Biarritz, France, May 1995. Chapters 1 and 3, and Table of Contents.
Product Specification–Scutellariae Extract–Nov. 18, 1994.

*Primary Examiner*—Shelly A. Dodson
*Attorney, Agent, or Firm*—Karen A. Lowney, Esq.

[57] ABSTRACT

The present invention relates to nonchemical sunscreen composition comprising as its active components, in synergistically effective amounts, a plant extract containing at least about 50% by weight of proanthocyanidins, γ-oryzanol, ferulic acid and/or an ester thereof, titanium dioxide and optionally, Scutellaria extract.

29 Claims, No Drawings

NON-CHEMICAL SUNSCREEN COMPOSITION

FIELD OF THE INVENTION

The invention relates to compositions which provide protection for human skin against the sun. In particular, the invention relates to natural, non-chemical products which act as an effective sunscreen in such compositions.

BACKGROUND OF THE INVENTION

It has now long been recognized that the sun's rays can be extremely harmful to skin. The effects of overexposure to the sun, resulting specifically from ultraviolet radiation, range from short term effects, such as erythema(sunburn)to long-term effects, such as photoaging of the skin and skin cancer. With this awareness of the dangers associated with the sun, in a world where the benefits of regular exercise, often associated with outdoor activity, have also recently been emphasized, has evolved a compelling need for skin treatments or compositions which allow an individual a reasonable amount of sun exposure while providing adequate protection In recent years a number of different sunscreening agents have become available. There are opaque materials, such as zinc oxide and titanium dioxide, which literally provide a physical barrier to the penetrating rays of the sun. There are also a number of chemical materials which act by absorbing UV light, such as cinnamates, aminobenzoic acids or derivatives thereof, benzophenones, anthranilates, and benzyl or homomenthyl salicylate. Despite the plethora of sunscreening agents available, however, the search continues for new and improved sunscreens. One of the driving forces behind the continued search is the public's increasing demand for "natural" products, i.e., naturally occurring materials which can perform the same or similar functions to the synthetic chemicals which have been so frequently used in the past. Many have reported irritation or allergic reactions resulting from contact with one or another of the available sunscreens, particularly chemical agents. However, although there are naturally occurring materials which do provide a measure of sun protection, it has been frequently observed that the level of protection(e.g., the skin protection factor, or SPF) is inadequate to permit prolonged exposure to sun(see for example, U.S. Pat. No. 5,256,404).

Thus, there is a continuing demand for a "natural" sunscreen which will provide the same quality of sun protection as the available physical or chemical sunscreens. The present invention now provides a composition, the active ingredients of which are all naturally occurring, and which provides a level of protection which is equivalent to many of the currently available sunscreen products.

SUMMARY OF THE INVENTION

The present invention relates to a sunscreen composition comprising as its active components, in synergistically effective amounts, a plant extract containing at least about 50% proanthocyanidins, γ-oryzanol, ferulic acid and/or an ester thereof, titanium dioxide and optionally Scutellaria extract. It has unexpectedly been found that the combination of these components, in relatively small quantities, produces an SPF considerably higher than either the SPF factor of each one alone, or the SPF which would be expected as an additive effect of the cumulative SPFs of each individual component. In a preferred embodiment, the SPF of the composition is at least about 15, and preferably higher.

The invention also relates to a method of protecting skin against sun damage which comprises applying to the skin a protective amount of a composition comprising as its active components, in synergistically effective amounts, a plant extract containing at least about 50%; proanthocyanidins, γ-oryzanol, ferulic acid and/or an ester thereof, and optionally Scutellaria extract.

DETAILED DESCRIPTION OF THE INVENTION

Each of the components of the present composition are "non-chemical" products in that they are obtainable directly from naturally occurring material, and are routinely prepared from such material, or are readily purchased from commercial sources. For example, proanthocyanidins are found in a number of different types of plant extracts. Methods for preparation of proanthocyanidin containing extracts are described, for example, in U.S. Pat. Nos. 3,456,407 and 4,698,360; JP 63267774; JP 01042479; JP 6049053; WO 9013304; and EP 348781, the contents of which are incorporated herein by reference. For purposes of the present invention, however, it is important that the plant extract employed contain a relatively high percentage of proanthocyanidins, as the mere presence of proanthocyanidins in an extract is not sufficient to confer the desired activity; for example, grapeseed extract, a material also known to contain proanthocyanidins, does not perform adequately. Therefore, it is particularly preferred that the proanthocyanidin content of the extract should be at least about 50%, more preferably at least about 60% most preferably at least about 65%. An example of plant material which provides the necessary high levels of proanthocyanidins is a conifer bark extract, in particular a pine bark extract. Such an extract can be prepared, for example, by grinding pine bark to a coarse powder and extracting with boiling water. Further concentration of active components can he achieved by salt-precipitation of the extract, filtration, ethyl acetate extraction of the filtrate, and chloroform precipitation. The primary chemical components of pine bark extracts are phenolcarbonic acids(such as caffeic acid, ferulic acid, p-coumaric acid, gallic acid, vanillic acid, or p-hydroxyl benzoic acid), free catechins, and polyphenols, in particular a large proportion of bioflavonoids, which include the proanthocyanidins. Particularly preferred is a pine bark extract comprising a high level of water-soluble, short-chain length(six or fewer component monomer units) procyanidins. Such an extract is commercially available under the trade name Pycnogenol® from M. W. International, Inc. Hillside, N.J. The latter is an extract from bark of the maritime pine, *Pinus maritima*.

The second component, γ-oryzanol, is an ester of ferulic acid and a terpene alcohol having the following formula:

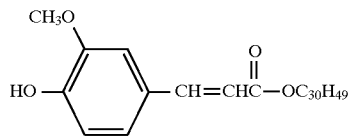

The compound is a component of rice bran oil, and is commercially available from a number of sources under the names oryzanol(Tsuno), Gamma oryzanol(Ikeda), or Oryzagamma-V(Ichimaru Pharcos).

The third component is *Scutellaria baicalensis* root extract. *Scutellaria baicalensis* is a perennial plant of the family Labiatea. The root extract also contains a large flavonoid component, including woogonin, baicalein, baicalin, and oroxylin-A. These compounds have the following formulae:

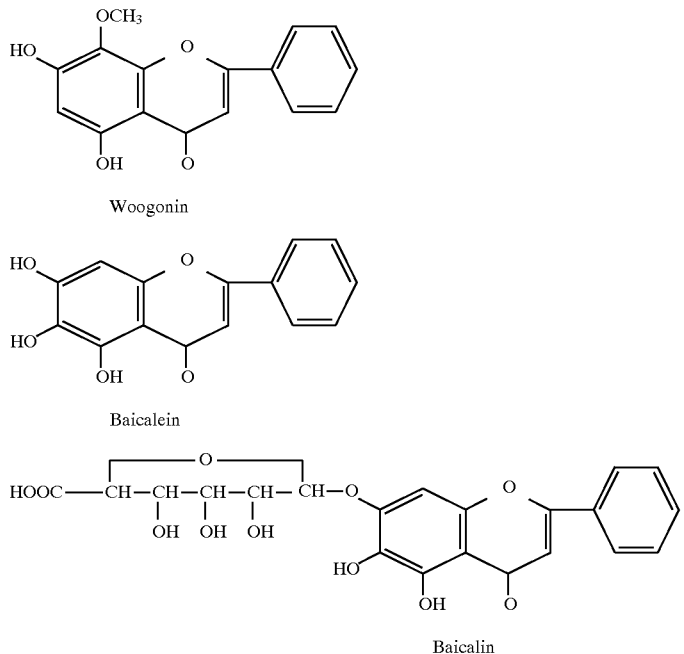

Woogonin

Baicalein

Baicalin

The material is available commercially as Ougon extract from Ichimaru Pharcos Co. Ltd, Japan).

Ferulic acid is a compound having the formula

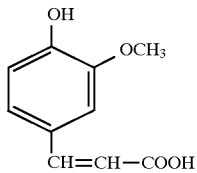

Ethyl ferulate is a naturally occurring ester of ferulic acid and ethyl alcohol having the following formula:

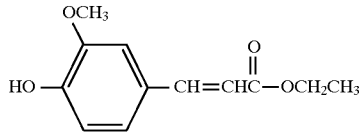

These compounds are found in a wide variety of plant extracts and are commercially available from Sigma(ferulic acid) or Ikeda(ethyl ferulate).

Titanium dioxide is a widely available material which is frequently used as a pigment in both cosmetics and paints.

The active components of the sunscreen formulations are well-known and have previously been disclosed as having biological activity. For example, proanthocyanidins have been shown to be potent antioxidants, and have been suggested for treatment of inflammation, cardiovascular disease, and a variety of other ailments(See, e.g., Report from The Second International Pycnogenol® Symposium, Biarritz, France, May 1995). Similarly, Scutellaria extract is a traditional Chinese medicine which also has antioxidant properties, and is suggested for use as an antiinflammatory, as a diuretic, and in the treatment of eczema. Ethyl ferulate is also used in cosmetics for its antioxidant properties. Oryzanol has been said to be useful in cholesterol reduction, as an antioxidant, and in stimulation of melanin synthesis. In fact, both pine bark extract and Scutellaria extract have been demonstrated as having UV absorbing activity, and have been suggested as providing a protective effect against the sun's rays, and titanium dioxide is widely used in a variety of SPF formulations. However, but for titanium dioxide, it appears that none of these products has previously been disclosed as having an SPF, and in fact, when tested for SPF properties, the observed SPF of each individual component, including titanium dioxide, is quite low, ranging only from less than 2 up to about 6(each value ±2).

Surprisingly, it has been found that, although the SPF of each component product is relatively unimpressive, when the components are combined, the combination product has an SPF considerably higher than would be expected, even from an additive effect of all four SPFs. In particular, the SPF of the combination of components is at least 15±2, preferably at least 19, and most preferably at least 20. Previously, such high level SPFs have been attained only with chemical sunscreens, or with a combination of chemical and nonchemical sunscreens. It has not previously been known to achieve an SPF as high as 19 from a combination of nonchemical sunscreen materials. The combination of these components thus has an unexpected synergistic, non-additive effect on the SPF of the composition as a whole. It is important to note that this effect is not simply a reflection of the combination of known UV filtering components, since tests conducted using combinations of other such known sunscreens, e.g., coffee bean extract, tea extract, and amino acids, with one or more of the components of the present invention fail to provide the same level of sun protection.

In a preferred embodiment, the proanthocyanidin containing material, for example, Pycnogenol™, which contains about 65% proanthocyanidins, is used in an amount of from about 0.1–5% by weight of the total composition; oryzanol, used in powder form, is present at about 0.5–10%, by weight; Scutellaria extract is present at about 0.05–3%, by weight; and ferulic acid, or ferulic acid ester such as ethyl ferulate, is present at about 0.5–20%; and an effective amount of titanium dioxide, preferably in micronized form, is from about 0.5–10%. It will be understood that these amounts are provided for guidance purposes, and may be varied; in particular, the upper limits may be increased, but with little or no concomitant improvement in performance. The combination of proanthocyanidin, oryzanol, ethyl ferulate, and titanium dioxide yields a composition having an SPF of at least 15($\pm$2), and the addition of Scutellaria extract can increase the SPF to 19($\pm$2) or higher.

The components of the present invention can be used in any form appropriate for use in sun protection. The components together are readily dissolved in aqueous solutions. For final product formulation, they may be combined with any compatible cosmetically or pharmaceutically acceptable carrier, for example, solutions, colloidal dispersions, emulsions, suspensions, creams, lotions, gels, foams, mousses and the like.

In a preferred embodiment, the carrier is a cream, lotion or emulsion. Formulations of this type are well known to the skilled artisan, and may be routinely prepared using art recognized techniques. In a particularly preferred embodiment, the formulation is an emulsion. An emulsion contains one or more oil components, an aqueous component, and a specific emulsifier component chosen depending on the nature of the desired emulsion.

The oil component may be any pharmaceutically or cosmetically acceptable material which is substantially insoluble in water. These materials can be found for example in the CTFA International Dictionary of Cosmetic Ingredients as well as the U.S. Pharmacopoeia or equivalent sources. Suitable oil components include, but are not limited to, natural oils, such as coconut oil; hydrocarbons, such as mineral oil and hydrogenated polyisobutene; fatty alcohols, such as octyldodecanol; esters, such as C12–15 alkyl benzoate; diesters, such as propylene glycol dipelargonate; triesters, such as glyceryl trioctanoate; sterol derivatives, such as lanolin; animal waxes, such as beeswax; plant waxes, such as carnauba; mineral waxes, such as ozokerite; petroleum waxes, such as paraffin wax; synthetic waxes, such as polyethylene; and mixtures thereof. Suitable oil components may also be silicones including, but not limited to, volatile silicones such as cyclomethicone; polymeric silicones such as dimethicone; alkylated derivatives of polymeric silicones, such as cetyl dimethicone and lauryl trimethicone; hydroxylated derivatives of polymeric silicones, such as dimethiconol; and mixtures thereof. The aqueous component refers to any pharmaceutically or cosmetically acceptable material consisting essentially or predominantly of water.

For preparation of an oil-in-water emulsion, the oil-in-water emulsifier will be an emulsifier having a hydrophilic-lipophilic balance(HLB) of at least 6, or a mixture of such emulsifiers with one or more water-in-oil emulsifiers(i.e., emulsifiers having an HLB of from about 2 to about 6), in which case the type and amount of each emulsifier present in the mixture is selected such that the effective HLB of the resultant oil-in-water emulsifier component is at least about 6. Techniques for combining and ascertaining the effective HLB of a mixture of emulsifiers are known; see L. M. Prince, in M. G. DeNavarre, "The Chemistry and Manufacture of Cosmetics", VolumeIII, Second Ed., (Continental Press, Orlando, 1975), pp. 25–37.

Suitable oil-in-water emulsifiers include, but are not limited to, sorbitol derivatives, such as sorbitan monolaurate and polysorbate 20; ethoxylated alcohols such as laureth-23, ethoxylated fatty acids such as PEG-1000 stearate; amidoamine derivatives such as stearamidoethyl diethylamine; sulfate esters such as sodium lauryl sulfate; phosphate esters such as DEA cetyl phosphate; fatty acid amine salts such as TEA stearate; and mixtures thereof.

The emulsion may also be a water-in-oil emulsion. For this purpose, a water-in-oil emulsifier is employed. This refers to any cosmetically acceptable emulsifier having an HLB of no greater than 6, preferably from about 2 to about 4. Suitable water-in-oil emulsifiers include, but are not limited to, sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2 lactylate; lecithin; and mixtures thereof.

Various other optional ingredients may be included in the compositions of the present invention, these include but are not limited to preservatives, emollients, antiseptics, pigments, dyes, humectants, propellants, as well as other classes of materials whose presence may be cosmetically, or medicinally desirable. Common examples can be found in the *CTFA International Cosmetic Ingredient Dictionary* 4th Edition, The Cosmetic, Toiletry, and Fragrance Association, Inc., Washington, D.C., 1991, as well as in *Remington's Pharmaceutical Sciences*, 18th Edition, A. R. Greenaro Ed., Mack Publishing Co., Easton, Pa., 1990. Common examples of such ingredients are provided below by way of example and not limitation.

Optional ingredients include emollients or humectants, such as glycerine or propylene glycol, mineral oil, petrolatum, fatty acid esters, such as myristal lactate, caprylic and capric triglycerides, dimethicone and natural whole oils or components thereof, moisturizing ingredients, such as wheat lipid extracts or ceramides, preservatives, such as methyl paraben, phenoxyethanol, BHT, BHA and the like.

In a particularly preferred embodiment, the formulation also contains one or more antioxidants, particularly lipid-soluble antioxidants, which can provide an additional level of protection against the effects of solar radiation. Suitable antioxidants for the present formulations include, but are not limited to, Vitamin E and derivatives thereof, such as tocopheryl acetate or linoleate; rosemary extract; and green tea extract.

The compositions of the present invention are used as would be any sun protection product, and therefore, the present invention also provides a method for protecting skin for the effects of the sun. The method comprises applying to the skin a protective amount of a composition comprising as its active components, in synergistically effective amounts, an appropriate proanthocyanidin-containing component, γ-oryzanol, titanium dioxide, ferulic acid and/or, and optionally Scutellaria extract. Such application is achieved in the same manner as with known sunscreen compositions, and will be readily understood by those of ordinary skill in the art. The method may be repeated as necessary depending upon the time of exposure to the sun and/or activities which may diminish the efficacy of the sunscreens, e.g., swimming, bathing, perspiration, etc.

The following non-limiting examples further illustrate the compositions of the invention.

Examples

Example 1

This example demonstrates the synergistic effect of the combination of the components of the present invention. Specifically, one or more of the components were prepared in a standard formulation, in various combinations. Table 1 demonstrates the various combinations and the resulting SPFs.

| COMPONENT (in wt. Percent) | FORMULA NUMBER | | | | | | |
|---|---|---|---|---|---|---|---|
| | 1 | 2 | 3 | 4 | 5 | 6 | 7 |
| ethyl ferulate | 3.0 | 3.0 | 3.0 | — | — | 3.0 | — |
| Pycnogenol ™ | 0.5 | 0.5 | 0.5 | — | 0.5 | — | — |
| Titanium dioxide | 2.0 | 2.0 | — | — | — | — | 2.0 |
| Scutellaria extract | — | 0.1 | 0.1 | 0.5 | — | — | — |
| oryzanol | 3.0 | 3.0 | 3.0 | 3.0 | 3.0 | 3.0 | 3.0 |
| SPF | 15 ± 2 | 19 ± 2 22 ± 2 24 ± 2 | 6 ± 2 | <2 | <2 | 8 ± 2 | 7 ± 2 |

The combinations in the composition of formulas 1 and 2 significantly outperform the other combinations, demonstrating the unexpectedly synergistic interaction of the components.

Example 2

The following illustrates a sunscreen formulation comprising the components of the invention:

| Material | % by weight |
|---|---|
| Phase I | |
| Castorwax MP-70 | 0.50 |
| Tocopherol linoleate | 0.90 |
| Phase II | |
| Pycnogenol ® | 0.50 |
| γ-oryzanol | 3.00 |
| Scutellaria extract | 0.10 |
| Titanium dioxide | 2.00 |
| Ethyl ferulate | 3.00 |
| Phase III | |
| cyclomethicone/dimethicone | 23.00 |
| cetyl dimethicone copolyol | 2.00 |
| blend of: polyglyceryl-4 isostearate cetyl dimethicone copolyol hexyl laurate | 1.00 |
| Phase IV | |
| deionized water | QS to 100 |
| 1,3 butylene glycol | 6.00 |
| methyl paraben | 0.25 |
| disodium EDTA | 0.10 |
| other ingredients | 0.80 |

To prepare the formulation, the wax of Phase I is melted and the other components dispersed in the wax with moderate mixing, while heated at 75–80° C. The Phase III ingredients are then added to phase I. The titanium dioxide, oryzanol and ethyl ferulate of Phase II are dispersed in Phase I and mixed well while maintaining the temperature at 80° C. Then the Phase IV ingredients, minus an amount of water adequate to make a solution of the Pycnogenol™ and Scutellaria extract, are also added to Phase I at 80° C. The Pycnogenol™ and Scutellaria extract of Phase II are dispersed in the portion of the water from Phase IV, then added to the other components in phase I.

What we claim is:

1. A sunscreen composition comprising as its active components (a)–(d), in synergistically effective amounts: (a) a plant extract containing at least about 50% by weight of proanthocyanidins, (b) γ-oryzanol, (c) ferulic acid and/or an ester thereof, (d) titanium dioxide; and optionally, (e) Scutellaria extract.

2. The composition of claim 1 in which the proanthocyanidin-containing extract contains at least about 60% proanthocyanidins.

3. The composition of claim 2 which is a conifer bark extract.

4. The composition of claim 3 in which the extract is an aqueous extract of *Pinus maritima*.

5. The composition of claim 2 in which the extract is present in an amount of from about 0.1–5% by weight of the total composition.

6. The composition of claim 1 in which the oryzanol is present in an amount of from about 0.5–10% by weight of the total composition.

7. The composition of claim 1 in which ferulic acid or an ester thereof is present in an amount of from about 0.5–20% by weight of the total composition.

8. The composition of claim 1 in which the titanium dioxide is present in an amount of from about 0.5–10% by weight of the total composition.

9. The composition of claim 1 in which Scutellaria extract is present in an amount of from about 0.5–3% by weight of the total composition.

10. The composition of claim 7 which contains from about 0.5–20% by weight of ethyl ferulate.

11. The composition of claim 1 which further comprises at least one additional antioxidant.

12. The composition of claim 11 in which the antioxidant is selected from the group consisting of rosemary extract, Vitamin E or a derivative thereof, and green tea extract.

13. A sunscreen composition comprising as its active components, about 0.1–5% conifer bark extract, about 0.5–10% γ-oryzanol, about 0.5–20% ethyl ferulate, and about 0.5–10% titanium dioxide.

14. The composition of claim 13 which further comprises about 0.05–3% Scutellaria extract.

15. The composition of claim 13 which comprises about 0.5–3% conifer bark extract, about 1–5% γ-oryzanol, about 1–10% ethyl ferulate, and about 0.5–5% titanium dioxide.

16. The composition of claim 15 which further comprises about 0.1–1% Scutellaria extract.

17. The composition of claim 16 which is in the form of an emulsion.

18. The composition of claim 1 which has an SPF of at least about 15.

19. The composition of claim 13 which has an SPF of at least about 15.

20. The composition of claim 14 which has an SPF of at least about 19.

21. The composition of claim 16 which has an SPF of at least about 19.

22. A method of protecting skin against sun damage which comprises applying to the skin a protective amount of a composition comprising as its active components (a)–(d), in synergistically effective amounts: (a) a plant extract containing at least about 50% proanthocyanidins, (b) γ-oryzanol, (c) ferulic acid and/or an ester thereof, (d) titanium dioxide; and optionally, (e) Scutellaria extract.

23. The method of claim 22 in which the proanthocyanidin-containing extract contains at least about 60% proanthocyanidins.

24. The method of claim 23 in which the extract is a conifer bark extract.

25. The method of claim 23 in which the extract is an aqueous extract of *Pinus maritima*.

26. A method of protecting skin against sun damage which comprises applying to the skin a protective amount of a composition according to claim 13.

27. A method of protecting skin against sun damage which comprises applying to the skin a protective amount of a composition according to claim 14.

28. A method of protecting skin against sun damage which comprises applying to the skin a protective amount of a composition according to claim 15.

29. A method of protecting skin against sun damage which comprises applying to the skin a protective amount of a composition according to claim 16.

* * * * *